United States Patent
Peru et al.

(10) Patent No.: US 9,632,021 B2
(45) Date of Patent: Apr. 25, 2017

(54) FAST QUANTITATIVE AND QUALITATIVE ANALYSIS OF SILICONE ADHESIVE

(71) Applicant: Colgate-Palmolive Company, New York, NY (US)

(72) Inventors: Deborah Ann Peru, Lebanon, NJ (US); Jason Nesta, Cedar Knolls, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/035,395

(22) PCT Filed: Oct. 23, 2014

(86) PCT No.: PCT/US2014/062067
§ 371 (c)(1),
(2) Date: May 9, 2016

(87) PCT Pub. No.: WO2015/069471
PCT Pub. Date: May 14, 2015

(65) Prior Publication Data
US 2016/0290920 A1 Oct. 6, 2016

Related U.S. Application Data

(60) Provisional application No. 61/901,927, filed on Nov. 8, 2013.

(51) Int. Cl.
G01N 21/3577 (2014.01)
G01N 21/35 (2014.01)
G01N 21/3563 (2014.01)
G01N 21/359 (2014.01)

(52) U.S. Cl.
CPC ......... *G01N 21/3577* (2013.01); *G01N 21/35* (2013.01); *G01N 21/359* (2013.01); *G01N 21/3563* (2013.01); *G01N 2201/129* (2013.01); *G01N 2201/12746* (2013.01)

(58) Field of Classification Search
CPC .. H01L 27/281; G01N 21/3563; G01N 21/35; G01N 21/359; G01N 21/3577; G01N 2201/129; G01N 2201/12746
See application file for complete search history.

(56) References Cited

U.S. PATENT DOCUMENTS 9,001,335 B2  4/2015  Phillips et al.
2006/0024246 A1*  2/2006  Maitra ................ A61K 8/0208
424/49

(Continued)

OTHER PUBLICATIONS

ASTM D2979-01(2009), Standard Test Method for Pressure-Sensitive Tack of Adhesives Using an Inverted Probe Machine, ASTM International, West Conshohocken, PA, 2009, www.astm.org.

(Continued)

*Primary Examiner* — David Porta
*Assistant Examiner* — Faye Boosalis

(57) ABSTRACT

This application is directed to a fast method of quantitatively and qualitatively validating the amount of silicone adhesive in a composition comprising silicone adhesive and silicone polymer which comprises of testing a sample of the composition with near IR or mid IR spectroscopy. The method can be extended to analyzing the amount of silicone adhesive in an oral care composition.

16 Claims, 4 Drawing Sheets

(56) References Cited

U.S. PATENT DOCUMENTS

| | | | |
|---|---|---|---|
| 2012/0070362 A1* | 3/2012 | Harms | C01B 33/027 |
| | | | 423/349 |
| 2013/0193325 A1* | 8/2013 | Phillips | G01N 21/3504 |
| | | | 250/339.07 |
| 2014/0117238 A1* | 5/2014 | McCann | G01N 21/3504 |
| | | | 250/338.4 |

OTHER PUBLICATIONS

ASTM D3121-06, Standard Test Method for Tack of Pressure-Sensitive Adhesives by Rolling Ball (Withdrawn 2015), ASTM International, West Conshohocken, PA, 2006, www.astm.org.

International Search Report and Written Opinion in International Application No. PCT/US2014/062067, mailed Jan. 8, 2015.

Lipp, 1992, "Near-infrared spectroscopy of silicon-containing materials," Applied Spectroscopy Reviews 27(4):385-408.

BS EN 1945, "Self adhesive tapes. Measurement of quick stick", 1996, http://shop.bsigroup.com/ProductDetail/?pid=000000000000824992 , accessed online: May 6, 2016.

FTA 9 Loop Track Measurement, FINAT Test Methods Handbook, 2014, http://www.finat.com/Knowledge/FINAT-publications/Technical-Handbook.aspx , accessed online: May 6, 2016.

\* cited by examiner

FAST QUANTITATIVE AND QUALITATIVE ANALYSIS OF SILICONE ADHESIVE

CROSS-REFERENCE TO RELATED APPLICATIONS

This application is a national stage entry under 35 U.S.C. §371 of International Patent Application No. PCT/US2014/062067, filed 23 Oct. 2014, which claims priority to U.S. Provisional Patent Application Ser. No. 61/901,927, filed on 8 Nov. 2013, which are incorporated herein by reference.

BACKGROUND

Silicone adhesives are a critical component in product efficacy and are used to ensure long term retention in the oral cavity of active ingredients from oral care compositions. Given their importance as ingredients in oral care compositions, it is critical to have accurate quantitative and qualitative information about the silicone adhesive prior to their use in bulk manufacturing of an oral care composition.

A typical means of performing quantitative and qualitative tests on silicone adhesives is to measure the viscosity using a Brookfield viscometer. However, this procedure often provides great variances in the viscosity (even with small difference in instrumental parameters and hardware) of the sample which is not reflective of the entirety of the silicone adhesive batch.

Another means of performing quantitative and qualitative tests on silicone adhesives is to measure the tack ("stickiness") of the adhesive. Numerous well known tests have been described to measure tack, e.g. probe tack (ASTM D2979), rolling ball (ASTM D3121), loop tack (FTM 9), "quick stick" (BS EN 1945).

However, these tests also suffer from the vagaries of duration of contact, temperature, rate of testing and the skill of the tester.

Both viscosity and tack testing attempt to provide quantitative and qualitative data by measuring a physical property of the test sample. However, one of ordinary skill in the art could achieve the same viscosity or tack data by using an alternative compound/composition than with the silicone adhesive.

Another problem with the previously known test methods is the quantitative and qualitative testing can only extend to the batch of silicone adhesive itself; these tests could not be extended directly to provide quantitative or qualitative data about the end product (e.g. an oral care composition) where the silicone adhesive has been added as an ingredient. (note: the method is more difficult to use for measurement of finished products with a yield stress)

Lastly, manufacturers of silicone adhesives often provide general information about their proprietary products, but not specific information which could enable the end user to reverse engineer their products. As such, another challenge in performing quantitative and qualitative test on a silicone adhesive is to gain sufficient test data to qualify a batch of silicone adhesive without having access to the specific chemical structure of the silicone adhesive.

Therefore, there is still a need in the art for a simple and rapid test which provides improved quantitative and qualitative analysis of silicone adhesives which can also be extended to end products and can be provide sufficient analysis in the absence of specific structural data about the silicone adhesive.

BRIEF SUMMARY

Surprisingly, the problems of the state of the art can be solved by using molecular spectroscopy, wherein the vibrational fingerprint of a proprietary silicone adhesive is measured directly and is free from silicone diluent interferences. The method is capable of providing a qualitative analysis based on the vibrational fingerprint, and a quantitative prediction for the concentration of adhesive in a silicone diluent.

The method may be useful as a quality control method during processing, by the receiving party, or in developing a certificate of analysis for a silicone adhesive.

The method can also be used as a quality control method for the amount of silicone adhesive which was added during the process of making an oral care composition.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

BRIEF DESCRIPTION OF THE DRAWINGS

The present invention will become more fully understood from the detailed description and the accompanying drawings, wherein.

DETAILED DESCRIPTION

Figure 1:
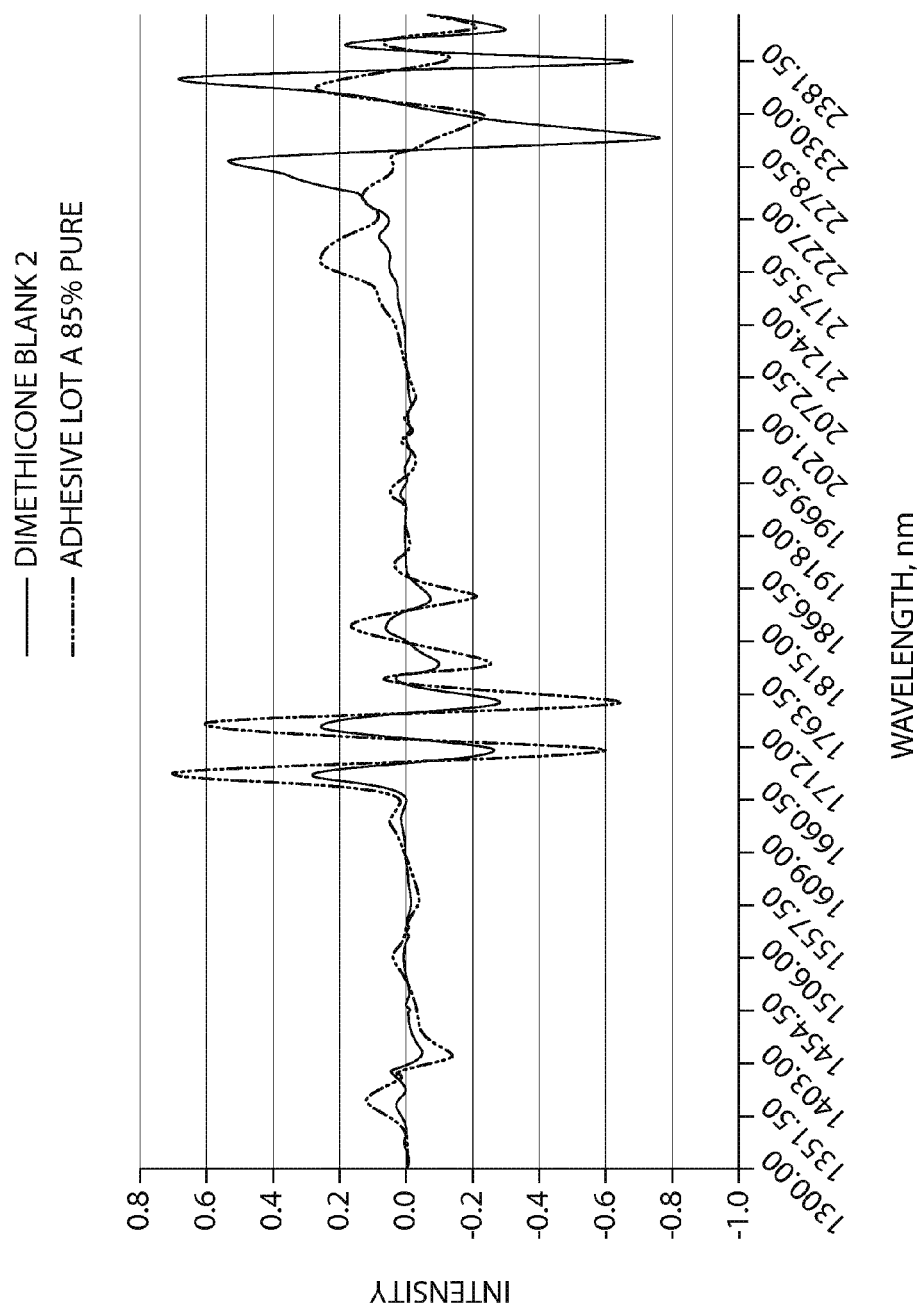
FIG. 1 depicts Near IR fingerprint showing regions that are specific for adhesive molecular vibrational overtones and combination bands

To address the problem of providing adequate quantitative and qualitative analysis to batches of silicone adhesive containing compositions, two IR methods were developing using the Near IR (2500 nm-1100 nm) and mid IR (4000 cm-1 to 650 cm-1) regions found in the electromagnetic spectrum.

Both methods were used to predict two different lots of silicone adhesive supplied by Dow Corning. The concentrations determined were within acceptable limits for an analytical test method. In addition, an out of specification lot was measured using the qualitative method to assess conformity with prior good lots.

One of the unique aspects of the Near IR method is that the method requires no clean up of the instrument. The samples are measured in flat and optically clear borosilicate glass vials using a diffuser that reflects light back to the detector. This makes analysis time extremely rapid. Total analysis time is less than one minute (approximately 30-35 seconds).

For the Mid IR method, a single bound diamond ATR (attenuated total reflectance) accessory is used that is able to be cleaned with petroleum distillates and dodecylbenzensulphonic acid. Once the adhesive is removed and solvent is applied, the ATR accessory can be cleaned and dried with dilute soap and water and alcohol. Total analysis time is about 2 minutes or less.

One embodiment of the invention is a method of validating the amount of silicone adhesive in a composition comprising silicone adhesive and silicone polymer, wherein the silicone adhesive and silicone polymer are not the same compound, which comprises of the steps of:
(a) making calibration standard compositions containing silicone adhesive and silicone polymer wherein at least one of said calibration standard compositions is within the range selected from the group consisting of within 1.0 wt. % and within 0.5 wt. % of the pre-determined acceptable range for the amount of silicone adhesive;
(b) optionally, subjecting the calibration standard compositions from step (a) to:
  (i) near IR spectroscopy; or
  (ii) mid IR spectroscopy;
wherein the IR spectra obtained from the calibration standard composition is used to form (1) a calibration curve representing the amount of silicone adhesive; and (2) an IR spectra fingerprint unique to the pre-determined acceptable range for the amount of silicone adhesive in the silicone adhesive and silicone polymer containing composition;
(c) obtaining a sample from a composition comprising silicone adhesive and silicone polymer;
(d) subjecting the sample from step (c) to:
  (i) near IR spectroscopy; or
  (ii) mid IR spectroscopy; and
comparing IR spectra obtained in step (d) with the calibration curve and IR spectra fingerprint from step (b), wherein a composition comprising silicone adhesive and silicone polymer is validated when having substantially the same pre-determined acceptable range for the amount of silicone adhesive as determined by the calibration curve and having substantially the same IR spectra fingerprint.

In another embodiment of the method described above, prior to step (a) a pre-determined acceptable range for the amount of silicone adhesive is established for the silicone adhesive and silicone polymer containing composition;

In another embodiment of the method described above, the method of validating is repeated for a different composition comprising silicone adhesive and silicone polymer with the exception of steps (a) and (b).

In another embodiment of the method described above, the amount of silicone adhesive and silicone polymers in the composition is selected from the group of wt. % consisting of greater than 90 wt. %, greater than 95 wt. %, greater than 99 wt. % and 100 wt. %, based on the total weight of the composition.

In another embodiment of the invention, the making of the calibration standard compositions containing silicone adhesive and silicone polymer wherein at least one of said calibration standard compositions is within 0.5 wt. % of the pre-determined acceptable range for the amount of silicone adhesive also includes making calibration standard compositions which have lesser and/or greater amounts of silicone adhesive relative to the pre-determined acceptable range; the lesser or greater amounts can be within ±50 wt. % of the pre-determined acceptable range.

In another embodiment of the invention, the making of the calibration standard compositions containing silicone adhesive and silicone polymer wherein more than one of said calibration standard compositions is within 1.0 wt. % of the pre-determined acceptable range and wherein the calibration standard composition is obtained from multiple lots/batches of the compositions containing silicone adhesive and silicone polymer.

In another embodiment of the method described above, the weight of the calibration standard composition is from 0.00001% to 1% of the weight of the composition comprising silicone adhesive and silicone polymer to be validated.

In another embodiment of the method described above, the silicone adhesive is selected from the group consisting of substituted polysiloxane or cross-linked substituted polysiloxane.

In another embodiment of the method described above, the silicone polymer is a polysiloxane or cross-linked polysiloxane.

Another embodiment of the invention is a method of determining the amount of silicone adhesive in an oral care composition which comprises:
a composition comprising silicone adhesive and silicone polymer, wherein the silicone adhesive and silicone polymer are not the same compound;
an active agent;
an orally acceptable carrier;
wherein the method comprises of the steps (a)-(d) described above and which further comprises:
(e) mixing the validated composition comprising silicone adhesive and silicone polymer from step (d) with an active agent and an orally acceptable carrier to form the oral care composition;
(f) obtaining a sample of the oral care composition from step (e) and subjecting it to:
  (i) near IR spectroscopy; or
  (ii) mid IR spectroscopy;
wherein the obtained IR spectra is compared against the calibration curve from step (b) to determine the amount of silicone adhesive in the oral care composition.

In another embodiment of the method described above, the amount of silicone adhesive in the oral care composition relative to the amount of silicone adhesive in the composition comprising silicone adhesive and silicone polymer is selected from the ranges consisting of 50 wt. % to less than 100 wt. %, 60 wt. % to 90 wt. % and 70 wt. % to 80 wt. %, based on the total weight of the oral care composition.

In another embodiment of the method described above, the silicone adhesive is selected from the group consisting of a substituted polysiloxane or cross-linked substituted polysiloxane.

In another embodiment of the method described above, the silicone polymer is selected from the group consisting of polysiloxane or cross-linked polysiloxane.

In another embodiment of the method described above, the active agent is selected from the group consisting of abrasives, amino acids, anti-bacterial agents, anti-plaque agents, bleaching agents, breath freshening agents, a fluoride ion source, stannous ion source, tartar control agent, whitening agents, zinc salts and mixtures thereof.

In another embodiment of the method described above, the active agent is a whitening agent selected from the group consisting of peroxide compounds, metal chlorites and persulfate.

In another embodiment of the method described above, the whitening agent is a peroxide compound, wherein the peroxide compound is hydrogen peroxide bound to polyvinylpyrrolidone.

Embodiments of the present invention are further described in the following examples. The examples are merely illustrative and do not in any way limit the scope of the invention as described and claimed.

EXAMPLES

Figure 2:
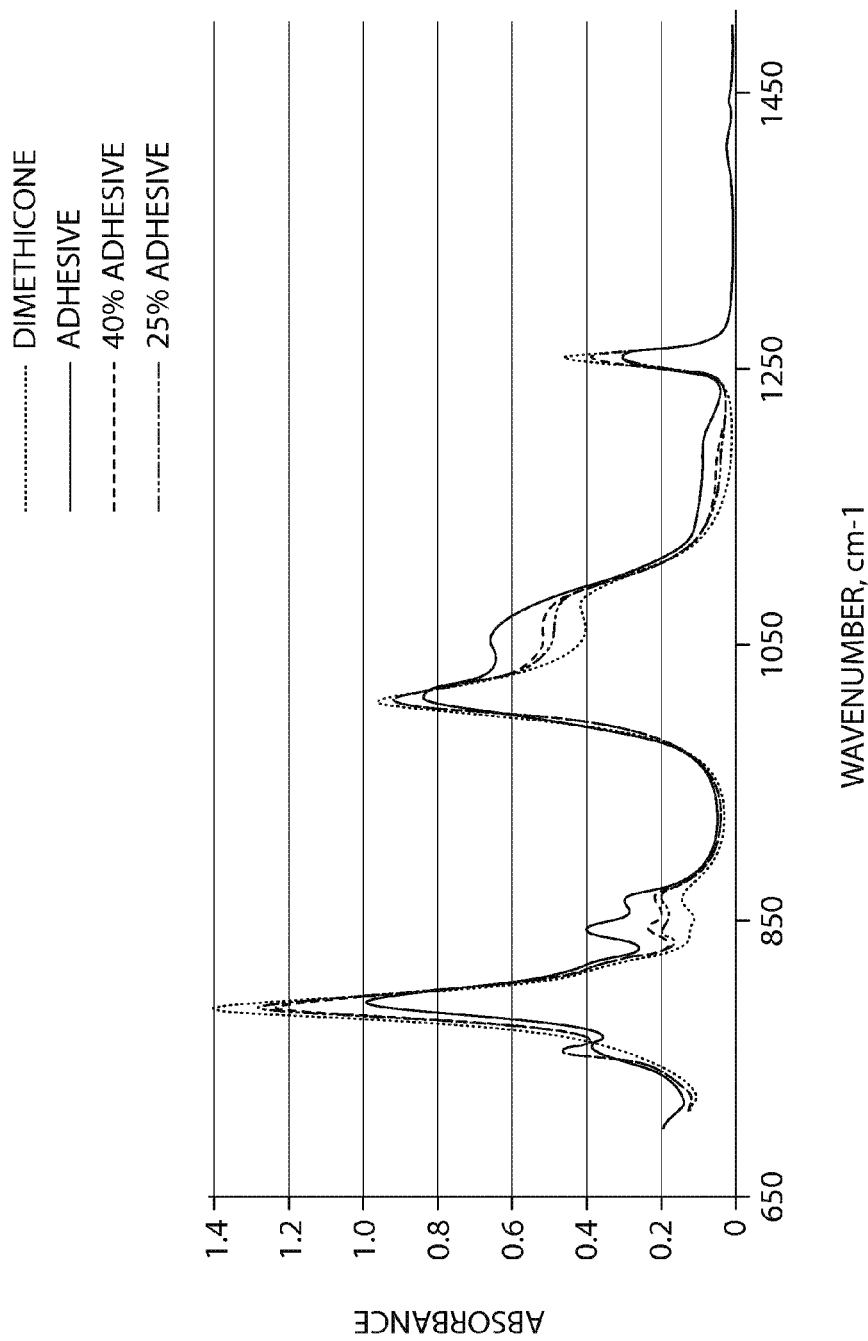
FIG. 2 depicts Mid IR fingerprint showing regions that are specific for adhesive fundamental molecular vibration caused by molecular stretching, bending, twisting, and wagging motions.

Experimental Details
Instrumentation (or Eqauivalent can be Used)
FOSS NIRSystems XDS Near IR with Rapid Solid Analyzer (range 2500 nm-400 nm)
Lead Sulfide Detector
1 mm pathlength diffusers
Measurement parameters: Fixed resolution, 32 co-added scans
Disposible VWR vials or Kimble Shell vials (Opticlear)
Perkin Elmer Spectrum 2000
Single bounce Diamond ATR
DTGS Detector
Measurement parameters: 4 cm−1×axis spacing, 16 co-added scans (can increase scan number for better signal/noise, but the measurement time will increase exponentially.
Preparation of Standards
(1) Record weight of silicone adhesive containing sample;
(2) Calculate weight of silicone required to dilute silicone adhesive sample to the pre-determined amount/range;
(3) Heat to 80° C.; and
(4) Mix for 15 minutes.
Calibration Standards
Seven Calibration Standard concentrations prepared for use in the quantitative method
Lot 025142-23A—[40.9%, 45.6%, 47.9%, 52.6%]
Lot 025142-23B—[29.7%, 40.9%, 52.6]
Blank—0% adhesive, 100% dimethicone (silicone)
Validation of Method with Three Factory Blended Samples Near 40%
0006700794, 025142-23A, 025142-23B
Quantitative and Qualitative Method Algorithms
The Near IR and Mid IR quantitative calibration was developed by correlating the regions with strong adhesive vibrational response to the concentrations prepared in the laboratory by weight (see FIGS. 1 and 2). Since the analytical balance was used to prepare the calibration standards, the IR is considered a primary method of detection when used for concentration determination. The calibration algorithm used is called partial least squares uses factor analysis to correlate the matrix of vibrational responses to the Y matrix of concentrations. Then uses a leave one out approach to optimize the number of terms in the model by predicting each of the standards as a true unknown when it is left out of the calibration. This method ensures the minimum number of terms (principal components) are used in the final calibration model thus avoiding overfitting the model with extraneous signal.

The Qualitative conformity methods were developed also by using the regions that are highly specific for adhesive. The method uses principal component analysis, an algorithm that only uses the vibrational fingerprint and ignores the concentration matrix. In developing a qualitative method, the calibration set typically contains samples that are known to be physically and chemically in specification. Thus, only the 40% samples should be used. Once a model is developed that maps the fingerprint and variability of the good samples, it can be used to predict the distance between a new lot of material and the good sample model. The prediction is reported in units of Mahalanobis distance and is analogous to an Euclidean distance or standard deviation.

Near IR Method Calibration Results

Figure 3:
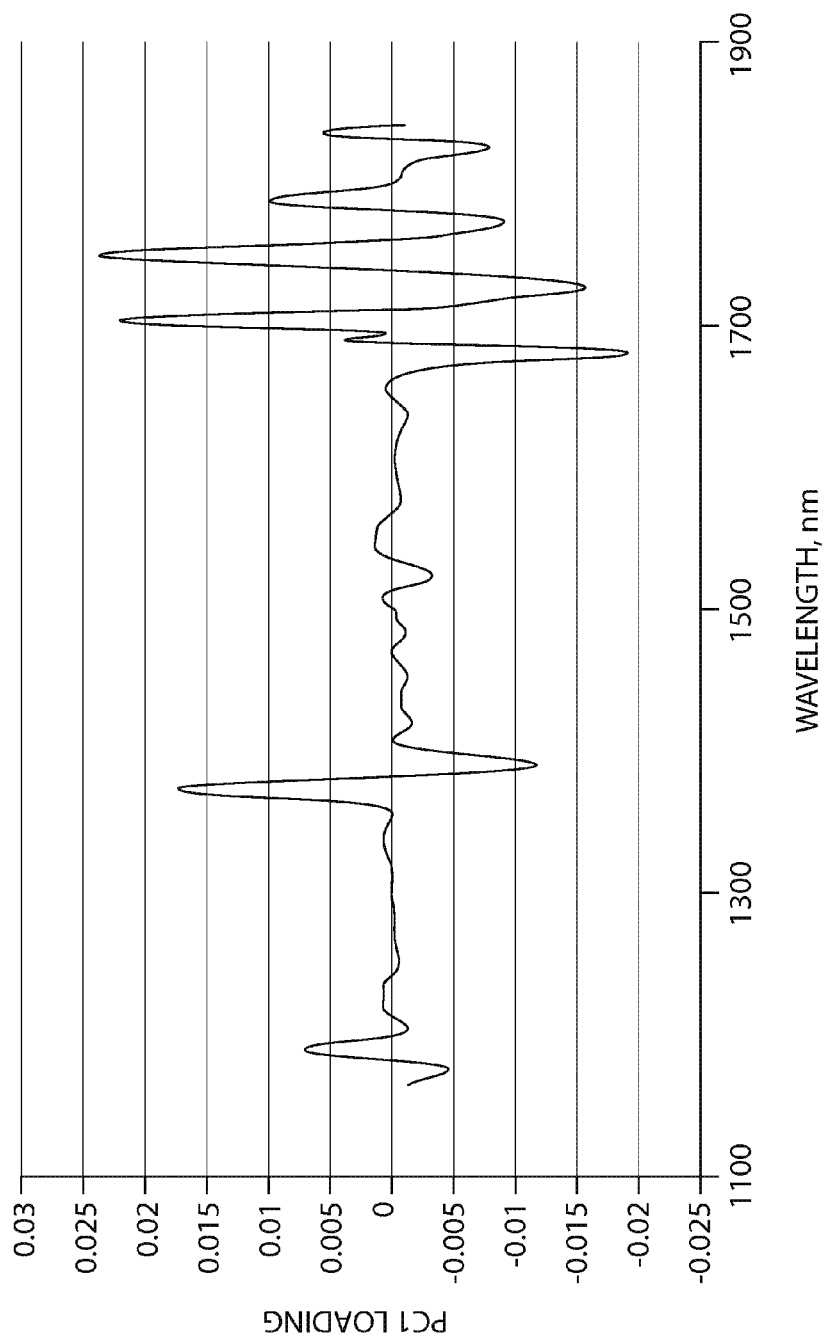
FIG. 3 depicts Near IR Calibration Fingerprint. Larger bands show stronger regions associated with concentration change.

The Near IR calibration results are found in FIG. 3 &Table 1. FIG. 3 shows the calibration fingerprint used to create the calibration curve. The strong bands are found near the OH (1400 nm) and CH (1700 nm) regions. The combination band region from 1900 nm to 2300 nm was not used to create the final calibration curve as it was found to introduce error due to nonlinear detector response.

Table 1 shows the final calibration curve which compares the actual amount of silicone adhesive in wt. % vs. the amount predicted using the near IR method; the data was obtained via PLS (partial least squares) regression analysis of Near IR fingerprint versus adhesive concentration. The plot shows the leave one out results (prediction vs. actual concentration).

The correlation between the spectra and concentration is >0.999 using 2 or 3 principal components (modeling terms) in the final equation.

TABLE 1

| Actual, wt. % | near IR predicted, wt. % |
|---|---|
| 45.6 | 45.74408 |
| 45.6 | 45.46407 |
| 29.7 | 30.45269 |
| 29.7 | 29.58430 |
| 52.6 | 52.96398 |
| 52.6 | 51.97949 |
| 40.9 | 40.68705 |
| 40.9 | 40.57164 |
| 47.9 | 48.18048 |
| 47.9 | 48.07057 |
| 52.6 | 52.48449 |
| 52.6 | 52.71365 |
| 40.9 | 40.36704 |
| 40.9 | 41.15752 |

Table 2 shows the validation results of various lots of 40% adhesive along with some of the outlier samples containing 85% adhesive, and 0% adhesive. The conformity index was marginal for detecting the difference between pure dimethicone and with adhesive but is able to quantify adhesive concentration differences between 0% % and 85% adhesive with good accuracy. The agreement between the determined concentrations and the actual concentrations was exceptional within the range of concentrations used to calibrate the instrument.

TABLE 2

| | Near IR Validation | | | |
|---|---|---|---|---|
| | | | Quantiative | |
| Sample | Qualitative <3 = pass Conformity | Pass/ Fail Limit | Actual, % | Near IR, % |
| Adhesive A | 1276 | Fail | 85 | >100 |
| Adhesive B | 1000 | Fail | 85 | >100 |
| dimethione blank | 3.3 | Fail | 0 | 2 |

TABLE 2-continued

Near IR Validation

| Sample | Qualitative <3 = pass Conformity | Pass/ Fail Limit | Quantiative | |
|---|---|---|---|---|
| | | | Actual, % | Near IR, % |
| dimethicone blank 2 | 3.3 | Fail | 0 | 1.7 |
| adhesive Lot 0006700794 40 rep1 | 1.33 | Pass | 40 | 40.6 |
| adhesive Lot 0006700794 40 rep2 | 1.36 | Pass | 40 | 40.2 |
| adhesive 40 lot 0125142-23 B rep1 | 0.85 | Pass | 40 | 39.7 |
| adhesive 40 let 0125142-23 B rep2 | 0.8 | Pass | 40 | 40.2 |
| adhesive 40 lot 0125142-23 A rep1 | 0.8 | Pass | 40 | 40.1 |
| adhesive 40 let 0125142-23 A rep2 | 0.73 | Pass | 40 | 40 |

Mid IR Method Calibration Results

Figure 4:
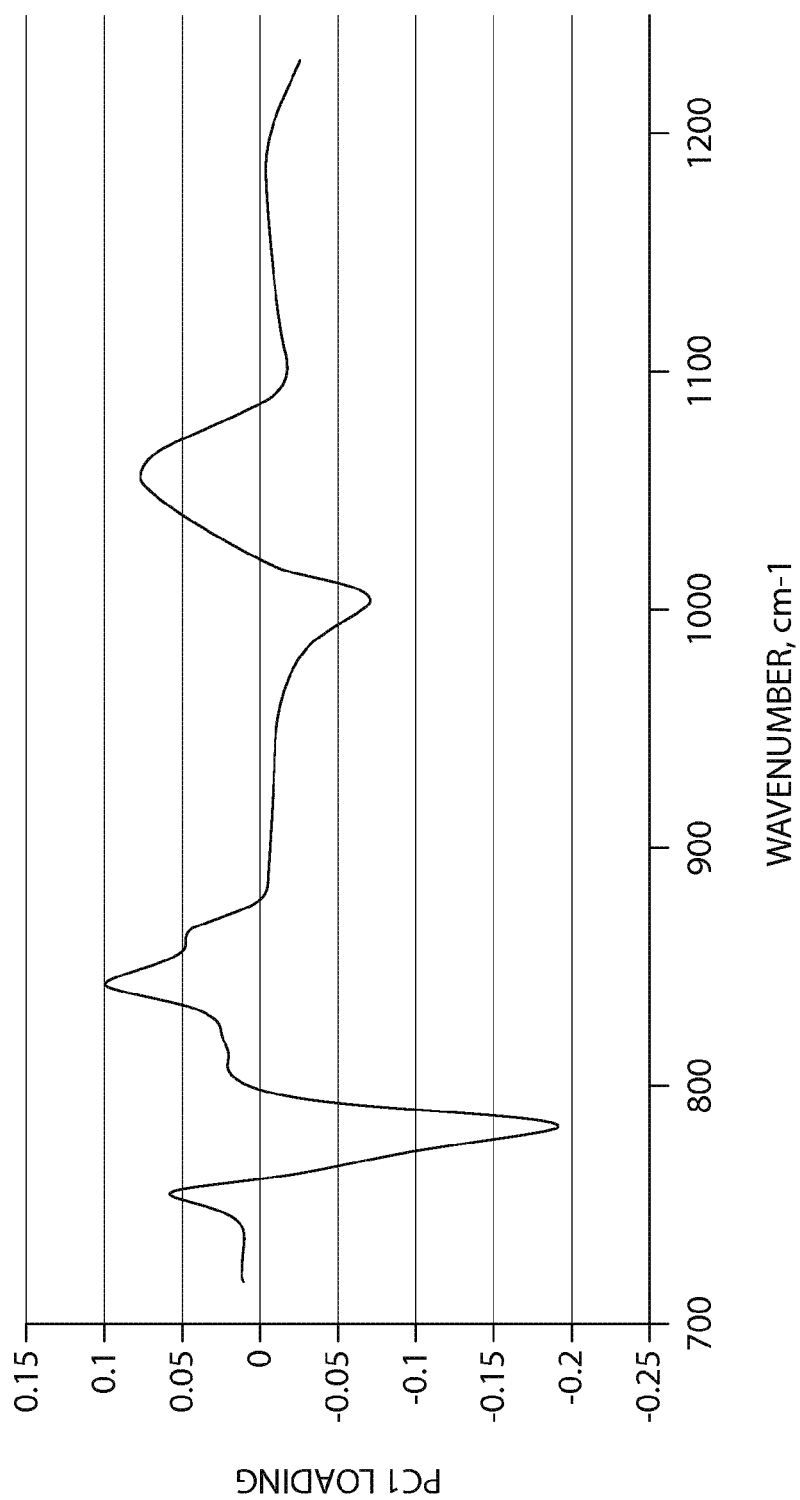
FIG. 4 depicts Mid IR Calibration Fingerprint. Larger bands show stronger regions associated with concentration change.

The calibration results for the Mid IR method is found in FIG. 4 & Table 3. FIG. 4 shows the calibration fingerprint used in the final equation. The bands showing the strongest intensity are the vibrational frequencies with the most weighting for prediction of adhesive concentration. As you can see a strong band exists near 790 cm−1.

Table 3 shows the final calibration curve which compares the actual amount of silicone adhesive in wt. % vs. the amount predicted using the mid IR method; the data was obtained via PLS (partial least squares) regression analysis of mid IR fingerprint versus adhesive concentration. With 2-3 principal components a correlation greater than 0.99 is obtained.

TABLE 3

| Actual, wt. % | mid IR predicted, wt. % |
|---|---|
| 40.9 | 40.89288 |
| 40 | 40.53328 |
| 47.9 | 47.01462 |
| 40.9 | 40.80682 |
| 52.6 | 52.75493 |
| 52.6 | 52.53996 |
| 45.6 | 44.97672 |
| 47.9 | 48.41198 |

Table 4 provides the validation evidence when using the method to predict the concentration of on-target adhesive samples and out of specification samples. The conformity prediction is found to be significantly out of specification compared with the specification limit of 3 for both the dimethicone and pure adhesive material. The concentrations determined were within expectation. The accuracy of measuring the 40% samples was excellent and comparable to the Near IR method. The Mid IR had a much larger conformity value for dimethicone, indicating that the specificity for detection of the presence of adhesive is better than Near IR.

TABLE 4

Validation results from Mid IR method

| Sample | Qualitative <3 = pass Conformity | Pass/ Fail Limit | Quantiative | |
|---|---|---|---|---|
| | | | Actual, % | MID IR, % |
| Adhesive A | >5000 | Fail | 85 | >90 |
| Adhesive B | >700 | Fail | 85 | >90 |
| adhesive Lot 0006700794 40 rep1 | 0.86 | Pass | 40 | 40.6 |
| adhesive 40 lot 0125142-23 B rep1 | 0.86 | Pass | 40 | 40.3 |
| adhesive 40 lot 0125142-23 A rep1 | 0.76 | Pass | 40 | 40.6 |
| Dimethicone | >300,000 | Fail | 0 | NA |

In conclusion, both the Mid IR and Near IR methods can be used ensure in-coming adhesive is chemically equivalent in concentration to the 40% concentration levels tested in early ship tested samples.

As those skilled in the art will appreciate, numerous changes and modifications may be made to the embodiments described herein without departing from the spirit of the invention. It is intended that all such variations fall within the scope of the appended claims.

We claim:

1. A method of quantitatively and qualitatively validating the amount of silicone adhesive in a composition comprising silicone adhesive and silicone polymer, wherein the silicone adhesive and silicone polymer are not the same compound, which comprises of the steps of:
    (a) making calibration standard compositions containing silicone adhesive and silicone polymer wherein at least one of said calibration standard compositions has the pre-determined acceptable range for the amount of silicone adhesive;
    (b) subjecting the calibration standard compositions from step (b) to:
        (i) near IR spectroscopy; or
        (ii) mid IR spectroscopy;
    wherein the IR spectra obtained from the calibration standard composition is used to form (1) a calibration curve representing the amount of silicone adhesive; and (2) an IR spectra fingerprint unique to the pre-determined acceptable range for the amount of silicone adhesive in the silicone adhesive and silicone polymer containing composition;
    (c) obtaining a sample from a composition comprising silicone adhesive and silicone polymer;
    (d) subjecting the sample from step (c) to:
        (i) near IR spectroscopy; or
        (ii) mid IR spectroscopy; and
    comparing IR spectra obtained in step (d) with the calibration curve and IR spectra fingerprint from step (b), wherein a composition comprising silicone adhesive and silicone polymer is validated when having substantially the same pre-determined acceptable range for the amount of silicone adhesive as determined by the calibration curve and having substantially the same IR spectra fingerprint.

2. The method of claim 1, wherein the method of validating is repeated for a different composition comprising silicone adhesive and silicone polymer with the exception of steps (a) and (b).

3. The method of claim 1, wherein the amount of silicone adhesive and silicone polymers in the composition is selected from the group of wt. % consisting of greater than 90 wt. %, greater than 95 wt. %, greater than 99 wt. % and 100wt. %, based on the total weight of the composition.

4. The method of claim 1, wherein the weight of the calibration standard composition is from 0.00001% to 1% of the weight of the composition comprising silicone adhesive and silicone polymer to be validated.

5. The method of claim 1, wherein the silicone adhesive is selected from the group consisting of substituted polysiloxane or cross-linked substituted polysiloxane.

6. The method of claim 1, wherein the silicone polymer is a polysiloxane or cross-linked polysiloxane.

7. The method of claim 1, wherein the validation time is less than one minute when the sample from step (d) is subjected to near IR spectroscopy.

8. The method of claim 1, wherein the validation time is less than two minutes when the sample from step (d) is subjected to mid IR spectroscopy.

9. The method of claim 1, wherein prior to step (a) a pre-determined acceptable range for the amount of silicone adhesive is established for the silicone adhesive and silicone polymer containing composition.

10. A method of quantitatively and qualitatively determining the amount of silicone adhesive in an oral care composition which comprises:
    a composition comprising silicone adhesive and silicone polymer, wherein the silicone adhesive and silicone polymer are not the same compound;
    an active agent;
    an orally acceptable carrier;
    wherein the method comprises of the steps of claim 1 and further comprises:
    (e) mixing the validated composition comprising silicone adhesive and silicone polymer from step (d) with an active agent and an orally acceptable carrier to form the oral care composition;
    (f) obtaining a sample of the oral care composition from step (e) and subjecting it to:
        (i) near IR spectroscopy; or
        (ii) mid IR spectroscopy;
    wherein the obtained IR spectra is compared against the calibration curve from step (b) to determine the amount of silicone adhesive in the oral care composition.

11. The method of claim 10, wherein the amount of silicone adhesive in the oral care composition relative to the amount of silicone adhesive in the composition comprising silicone adhesive and silicone polymer is selected from the ranges consisting of 50 wt. % to less than 100 wt. %, 60 wt. % to 90 wt. % and 70 wt. % to 80 wt. %, based on the total weight of the oral care composition.

12. The method of claim 10, wherein the silicone adhesive is selected from the group consisting of a substituted polysiloxane or cross-linked substituted polysiloxane.

13. The method of claim 10, wherein the silicone polymer is selected from the group consisting of polysiloxane or cross-linked polysiloxane.

14. The method of claim 10, wherein the active agent is selected from the group consisting of abrasives, amino acids, anti-bacterial agents, anti-plaque agents, bleaching agents, breath freshening agents, a fluoride ion source, stannous ion source, tartar control agent, whitening agents, zinc salts and mixtures thereof.

15. The method of claim 10, wherein the active agent is a whitening agent selected from the group consisting of peroxide compounds, metal chlorites and persulfate.

16. The method of claim 10, wherein the whitening agent is a peroxide compound, wherein the peroxide compound is hydrogen peroxide bound to polyvinylpyrrolidone.

* * * * *